United States Patent [19]

Andersson

[11] Patent Number: 6,116,094

[45] Date of Patent: Sep. 12, 2000

[54] METHOD FOR DETERMINING THE AXIAL LOAD ON AN ELONGATED MEMBER

[75] Inventor: Tobias Axel Andersson, Nacka, Sweden

[73] Assignee: Atlas Copco Controls AB, Nacka, Sweden

[21] Appl. No.: 09/043,595

[22] PCT Filed: Sep. 23, 1996

[86] PCT No.: PCT/SE96/01173

§ 371 Date: Mar. 20, 1998

§ 102(e) Date: Mar. 20, 1998

[87] PCT Pub. No.: WO97/11343

PCT Pub. Date: Mar. 27, 1997

[30] Foreign Application Priority Data

Sep. 22, 1995 [SE] Sweden .................................. 9503289

[51] Int. Cl.[7] ............................ G01N 3/00; G01N 29/98; G01H 13/00; G01L 1/25
[52] U.S. Cl. .............................................. 73/761; 324/635
[58] Field of Search .................................. 324/534, 637; 73/761, 574

[56] References Cited

U.S. PATENT DOCUMENTS

| | | |
|---|---|---|
| 3,975,948 | 8/1976 | Makino et al. . |
| 4,602,511 | 7/1986 | Holt . |
| 4,846,001 | 7/1989 | Kibblewhite . |
| 5,205,176 | 4/1993 | Kibblewhite ............................ 73/761 |
| 5,625,146 | 4/1997 | Hull .......................................... 73/574 |
| 5,719,503 | 2/1998 | Burnett ................................... 324/534 |

FOREIGN PATENT DOCUMENTS

| | | |
|---|---|---|
| 0 589 271 A1 | 3/1994 | European Pat. Off. . |
| WO 92/19983 | 11/1992 | WIPO . |

*Primary Examiner*—Josie Ballato
*Assistant Examiner*—Jim Nguyen
*Attorney, Agent, or Firm*—Frishauf, Holtz, Goodman, Langer & Chick, P.C.

[57] ABSTRACT

A method for determining the axial load on an elongate member by measuring the differences in time of flight for transversely and longitudinally ultrasonic waves introduced in the elongate member under a zero load condition and at a current temperature and the time of flight for both of these types of waves introduced into the elongate member under the actual load condition, and calculating from these differences in the time of flight the actual load on the elongate member taking into account the influence of any occurring difference in temperature of the elongate member between the zero load condition time of flight measurement and the actual load condition time of flight measurement.

6 Claims, No Drawings

METHOD FOR DETERMINING THE AXIAL LOAD ON AN ELONGATED MEMBER

This invention relates to a method for determining the axial load on an elongate member by means of ultrasonic waves.

In particular, the invention concerns a load determining method in which longitudinally as well as transversely directed ultrasonic waves are introduced at one end of an elongate member and the time of flight for these waves is individually measured.

Such a method is described in U.S. Pat. No. 4,602,511. This known method is based on the fact that the propagation speed dependency on stress is different between longitudinal waves and transverse waves.

A problem concerned with the above technique is that the time of flight varies with changing temperature in the object being inspected. The time of flight varies due to the fact that the propagation speed and the length of the object vary with the temperature. This results in an undesireable temperature related deviation in the calculated load acting on the object.

This is a problem in particular in assembling screw joints, because the temperature of the screw may differ to a large extent in the production environment. It is also very difficult to measure the temperature on each screw in mass production, and the tightening process itself generates heat in the screw.

A recent study verifies that there is a difference between longitudinal and transverse waves as regards the time of flight dependency on the temperature in the object being inspected. It has been found that the time of flight of transverse waves is more affected by temperature changes than longitudinal waves, whereas, oppositely, the time of flight for longitudinal waves is more dependent on the load magnitude than the time of flight for transverse waves.

This means that measured changes in flight time for the longitudinal and transverse waves provide information from which changes in temperature and load can be calculated.

The invention comprises a method for determining the actual load on an elongate member by measuring during a first, preliminary zero-load inspection stage the time of flight for longitudinal and transverse ultrasonic waves introduced into the elongate member for determining the zero-load length of the elongate member by measuring the time of flight (TOF) for both types of waves measuring during a second inspection stage the time of flight (TOF) for both type of waves under the actual load and temperature condition of the elongate member, comparing the time of flight (TOF) for the introduced waves measured at the zero-load condition with the time of flight (TOF) measured at the actual load and temperature condition, and calculating the actual load magnitude under compensation for the difference in temperature between the actual load and zero-load conditions.

In a practical application of the method according to the invention the transverse and longitudinal waves are introduced into the elongate member by means of an ultrasonic transducer of the type which is permanently attached to an end surface of the elongate member. Such a transducer is described in U.S. Pat. No. 5,205,176.

For carrying out the method according to the invention, there is needed the following physical data of the elongate member:

$T_0$ (K) An arbitrary temperature at which $v_{LC}$ and $v_{SO}$ are measured, should be set to about room temperature.

$v_{LO}$ (m/s) Velocity of the longitudinal wave at temperature $T_0$.

$v_{SO}$ (m/s) Velocity of the transverse (shear) wave at temperature $T_0$.

$K_{ST}$ (s/Km) Relative time of flight change for the transverse wave due to a change in temperature.

$K_{LT}$ (s/Km) Relative time of flight change for the longitudinal wave due to a change in temperature.

$K_{SL}$ (s/Nm) Relative time of flight change for the transverse wave due to a change in tensile load.

$K_{LL}$ (s/Nm) Relative time of flight change for the longitudinal wave due to a change in tensile load.

The above mentioned data must be collected for each application as they depend on both the material properties and the geometry (area) of for instance a screw in a screw joint application.

The following data measured at the time for the tightening:

$t_{SO}$ (s) Zero load TOF for the transverse wave.

$t_{LO}$ (s) Zero load TOF for the longitudinal wave.

$t_{SL}$ (s) TOF for the transverse wave in the loaded case.

$t_{LL}$ (s) TOF for the longitudinal wave in the loaded case.

and the following may be calculated therefrom:

$\Delta T$ (K) Deviation in temperature from $T_0$ at zero-load.

$\Delta T_L$ (K) Deviation in temperature from $T_C$ in the loaded case.

L (N) The tensile load in the fastener.

$l_0$ (m) Then length of the screw in zero-load at $T_0$.

In the initial stage of the tightening of a screw joint a zero-load measurement is made. From that information it is possible to determine the length (and the temperature) of the screw as follows:

Input $v_{LO}$ $v_{SO}$ $K_{ST}$ $K_{LT}$ $t_{SO}$ $t_{LO}$ L(=0)

Output: $l_0$ $\Delta T$

Solution:

The zero-load TOF ($t_{SO}$ and $t_{LO}$) must be equal to the zero-load TOF at $T_0$ with a temperature correction factor added:

$$t_{SO} = \frac{l_0}{v_{SO}} + l_0 K_{ST} \Delta T \tag{1}$$

$$t_{LO} = \frac{l_0}{v_{LO}} + l_0 K_{LT} \Delta T \tag{2}$$

$\Delta T$ is then extracted from (1):

$$\Delta T = \frac{1}{K_{ST}} \left( \frac{t_{SO}}{l_0} - \frac{1}{v_{SO}} \right) \tag{3}$$

(3) in (2) gives:

$$\frac{l_0}{v_{LO}} + \frac{K_{LT} \left( t_{SO} - \frac{l_0}{v_{SO}} \right)}{K_{ST}} = t_{LO} \tag{4}$$

$l_0$ is then extracted from (4):

$$l_0 = \frac{v_{LO} v_{SO} (t_{LO} K_{ST} - t_{SO} K_{LT})}{v_{SO} K_{ST} - v_{LO} K_{LT}} \tag{5}$$

If the actual temperature is needed it can be obtained from $T_0 + \Delta T$ where $\Delta T$ is extracted from (5) in (3):

$$\Delta T = \frac{t_{SO}v_{SO} - v_{LO}t_{LO}}{v_{LO}v_{SO}(t_{LO}K_{ST} - t_{SO}K_{LT})} \quad (6)$$

The next step is to calculate the axial load on the screw using the length and the TOF data. As we know the original length of the screw we can make a new temperature compensation, thereby eliminating the problem with heating due to tightening.

Input: $v_{LO}$ $v_{SO}$ $K_{ST}$ $K_{LT}$ $K_{SL}$ $K_{LL}$ $l_0$ $t_{SL}$ $t_{LL}$
Output: L $\Delta T_L$
Solution:

The difference in TOF from a zero-load measurement at $T_0$ can be divided into a load induced change and a temperature induced change, hence:

$$\left(t_{SL} - \frac{l_0}{v_{SO}}\right) = l_0(\Delta T_L K_{ST} + L K_{SL}) \quad (7)$$

$$\left(t_{LL} - \frac{l_0}{v_{LO}}\right) = l_0(\Delta T_L K_{LT} + L K_{LL}) \quad (8)$$

From (7) $\Delta T$ is extracted:

$$\Delta T_L = \frac{l}{K_{ST}}\left(\frac{t_{SL}}{l_0} - \frac{l}{v_{SO}} - L K_{SL}\right) \quad (9)$$

From (9) in (8) the actual load on the screw can be extracted:

$$L = \frac{K_{ST}v_{SO}(t_{LL}v_{LO} - l_0) + K_{LT}v_{LO}(t_{SL}v_{SO} - l_0)}{v_{SO}v_{LO}l_0(K_{LL}K_{ST} - K_{LT}K_{ST})} \quad (10)$$

$$\Delta T_L = \frac{K_{SL}v_{SO}(v_{LO}t_{LL} - l_0) + K_{LL}v_{LO}(v_{SO}t_{SL} - l_0)}{v_{LO}v_{SO}l_0(K_{LT}K_{SL} - K_{LL}K_{ST})} \quad (11)$$

The method according to the invention is suitable for but not limited to screw tightening applications. It may also be useful in:

All types of ultrasonic stress measurements where compensation for temperature changes is important.
Monitoring stress and temperature simultaneously in safety applications like:
pressure vessels
nuclear reactors etc.

In screw tightening applications, the described method may be use to control the power wrench during the tightening process. The ultrasonic transducer used for introducing the transverse and longitudinal waves in the screw is connected to an electronic operation control unit associated with the screw tightening tool.

In practical use of the invention as described above, it is desireable to use an ultrasonic transducer of the type being permanently attached to the end surface of the screw.

Alternatively, the method may be used for inspection of the prevailing load in previously tightened screw joints.

I claim:

1. Method for determining the axial load on an elongate member for which the physical data are registered, comprising the steps of introducing longitudinally as well as transversely directed ultrasonic waves at one end of the elongate member under a zero-load condition and at a current temperature, measuring individually the times of flight for said longitudinally and transversely directed waves through the elongate member at said zero-load condition, and calculating from the physical data of the elongate member and from the measured times of flight of said longitudinal and transverse waves the nominal length of the elongate member, introducing longitudinal as well as transverse waves into the elongate member under the actual load condition, comparing said times of flight measured under the actual load condition with said times of flight measured under said zero-load condition, and determining from the difference in the wave flight times the actual load on the elongate member taking into account the influence of any occurring difference in temperature of the elongate member between said zero-load measurement occasion and the actual load measurement occasion by the equation:

$$L = \frac{K_{ST}v_{SO}(t_{LL}v_{LO} - l_0) + K_{LT}v_{LO}(t_{SL}v_{SO} - l_0)}{v_{SO}v_{LO}l_0(K_{LL}K_{ST} - K_{LT}K_{ST})}$$

(where $v_{LO}$ is the velocity of the longitudinal waves at temperature $T_0$, $v_{SO}$ is the velocity of the transverse (shear) waves at temperature $T_0$, $K_{ST}$ is the relative time of flight change for the transverse waves due to a change in temperature, $K_{LT}$ is the relative time of flight change for the longitudinal waves due to a change in temperature, $K_{SL}$ is the relative time of flight change for the transverse waves due to a change in tensile load, $K_{LL}$ is the relative time of flight change for the longitudinal waves due to a change in tensile load, $t_{SL}$ is the time of flight for the transverse waves in the actual load condition, $t_{LL}$ is the time of flight for the longitudinal waves in the actual load condition, $l_0$ is the length of the elongate member in the zero-load condition at the temperature $T_0$).

2. Method according to claim 1, wherein said transverse and longitudinal waves are introduced into the elongate member by means of an ultrasonic transducer which permanently attached to an end surface of the elongate member.

3. Method according to claim 2, wherein said longitudinal and transverse waves are continuously or repeatedly introduced in one or more elongate members forming part of a joint, further comprising:

measuring continuously or repeatedly the time of flight of said longitudinally and transversely directed waves, and comparing said time of flight measurements with preceding time of flight measurements for monitoring continuously or repeatedly occurring changes in the actual load on said elongate member or members at varying temperatures.

4. Method according to claim 1 for determining the axial load on a screw in a threaded joint, wherein an ultrasonic transducer is coupled on one hand to said screw for introducing therein said transverse and longitudinal waves and on the other hand to an electronic operation control unit of a screw tightening tool including means for determining the actual load on said screw during tightening.

5. Method according to claim 4, wherein said transverse and longitudinal waves are introduced into said screw by means of an ultrasonic transducer which is permanently attached to an end surface of said screw.

6. Method according to claim 1, wherein said longitudinal and transverse waves are continuously or repeatedly introduced in one or more elongate members forming part of a joint, further comprising:

measuring continuously or repeatedly the time of flight of said longitudinally and transversely directed waves, and comparing said time of flight measurements with preceding time of flight measurements for monitoring continuously or repeatedly occurring changes in the actual load on said elongate member or members at varying temperatures.

* * * * *

UNITED STATES PATENT AND TRADEMARK OFFICE
CERTIFICATE OF CORRECTION

PATENT NO. : 6,116,094
DATED : September 12, 2000
INVENTOR(S) : Tobias Axel Lindback Page 1 of 1

It is certified that error appears in the above-identified patent and that said Letters Patent is hereby corrected as shown below:

<u>Title page,</u>
Item [75] Inventor, change "Andersson" to -- Lindbäck --.

Signed and Sealed this

Second Day of October, 2001

*Attest:*

*Nicholas P. Godici*

*Attesting Officer*

NICHOLAS P. GODICI
*Acting Director of the United States Patent and Trademark Office*